(12) United States Patent
Baumann et al.

(10) Patent No.: US 6,194,534 B1
(45) Date of Patent: Feb. 27, 2001

(54) ORGANOPOLYSILOXANES WITH DYE RESIDUES

(75) Inventors: Frank Baumann, Mehring; Gunter Mahr; Bernward Deubzer, both of Burghausen, all of (DE)

(73) Assignee: Wacker-Chemie GmbH, München (DE)

( * ) Notice: Subject to any disclaimer, the term of this patent is extended or adjusted under 35 U.S.C. 154(b) by 0 days.

(21) Appl. No.: 09/380,977

(22) PCT Filed: Mar. 12, 1998

(86) PCT No.: PCT/EP98/01413

§ 371 Date: Sep. 20, 1999

§ 102(e) Date: Sep. 20, 1999

(87) PCT Pub. No.: WO98/40429

PCT Pub. Date: Sep. 17, 1998

(30) Foreign Application Priority Data

Mar. 13, 1997 (DE) .............................. 197 10 461

(51) Int. Cl.$^7$ .......................... C08G 77/26; C08G 77/392
(52) U.S. Cl. ................................ 528/25; 528/28; 528/27; 528/38; 528/30; 534/651
(58) Field of Search .................................. 528/28, 25, 27, 528/38, 30; 534/651

(56) References Cited

U.S. PATENT DOCUMENTS

| | | |
|---|---|---|
| 2,925,313 | 1/1960 | Bailey et al. . |
| 4,403,099 | 9/1983 | Hirsch et al. . |
| 4,962,177 | * 10/1990 | Lo . |
| 5,281,240 | 1/1994 | McGee . |
| 5,831,080 | 11/1998 | Sejpka et al. . |

FOREIGN PATENT DOCUMENTS

| | | |
|---|---|---|
| 2088738 | * 8/1993 | (CA) . |
| 0 274 185 | 7/1988 | (EP) . |
| 0 283 206 | 9/1988 | (EP) . |
| 0 336 709 | 10/1989 | (EP) . |
| 0 455 384 | 11/1991 | (EP) . |
| 0 554 863 | 8/1993 | (EP) . |
| 0 612 759 | 8/1994 | (EP) . |
| 2 018 804 | 10/1979 | (GB) . |

OTHER PUBLICATIONS

English Abstract Corresponding to EP 0554863.
Journal of the Society of Dyers and Colourists, vol. 85, Sep. 1969, No. 9, pp. 440–405.

* cited by examiner

Primary Examiner—Robert Dawson
Assistant Examiner—Kuo-Liang Peng
(74) Attorney, Agent, or Firm—Brooks & Kushman P.C.

(57) ABSTRACT

The invention relates to organopolysiloxanes with dye residues comprising units of the general formula $$R^1{}_a(RO)_b A_c R^2{}_d SiO_{(4-a-b-c-d)/2} \qquad (I)$$

wherein R can be identical or different and is hydrogen atom or monovalent, substituted or unsubstituted hydrocarbon radical, $R^1$ can be identical or different and is hydrogen atom or monovalent, SC-bonded hydrocarbon radical, $R^2$ can be identical or different and is substituted, monovalent, Si—C bonded hydrocarbon radical, A can be identical or different and is a radical of a water-soluble organic dye containing at least one of sulfonic acid groups, sulfonate groups, or metal complexes thereof, a is 0, 1, 2, or 3, b is 0, 1, 2 or 3, d is 0, 1, 2, or 3 and c is 0, 1 or 2 with the proviso that the sum of a, b, c and d is less than or equal to 3, the organopolysiloxanes have at least one radical, and, in the units of the formula (I) where c is other than 0, d is 0.

10 Claims, No Drawings

ORGANOPOLYSILOXANES WITH DYE RESIDUES

The invention relates to functionalized silicone compounds with chromophoric molecules additionally attached covalently to them, to processes for their preparation and to the use of these colored silicone compounds.

The simultaneous use of silicone compounds and dyes is hampered by the immiscibility or insolubility of the majority of dyes in silicone compounds. In order to solve this problem, therefore, special blends of dyes with silanes or siloxanes are used, as described for example in U.S. Pat. No. 5,281,240. A further possibility for avoiding this incompatibility is the covalent attachment of dyes to silanes, as is described for example in J. Soc. Dyers and Col. 85, 1969, No. 9, 401-4. U.S. Pat. No. 2,925,313 and U.S. Pat. No. 4,403,099 describe dye-bearing siloxanes. These compounds, however, owing to their preparation processes, such as azo coupling or basic epoxy opening, are restricted to only one class of dye, such as aniline-containing azo compounds or aromatic compounds which carry nitro substituents, and/or to only epoxy-functionalized siloxanes. In addition, these siloxanes do not carry any other functional groups in the polymer chains.

The present invention provides organopolysiloxanes with dye radicals, comprising units of the general formula

$$R^1_a(RO)_b A_c R^2_d SiO_{(4-a-b-c-d)/2} \qquad (I)$$

in which

R can be identical or different and is hydrogen atom or monovalent, substituted or unsubstituted hydrocarbon radical, $R^1$ can be identical or different and is hydrogen atom or monovalent, SiC-bonded hydrocarbon radical, $R^2$ can be identical or different and is substituted, monovalent, SiC-bonded hydrocarbon radical, A can be identical or different and is the radical of a water-soluble organic dye, containing sulfonic acid groups and/or sulfonate groups, and/or of its complex compound with metals, a is 0, 1, 2 or 3, b is 0, 1, 2 or 3, d is 0, 1, 2 or 3, preferably 0 or 1, and c is 0, 1 or 2, preferably 0 or 1, with the proviso that the sum of a, b, c and d is less than or equal to 3, the organopolysiloxanes have at least one radical A per molecule, and in the units of the formula (I) where c is other than 0, d is 0.

In the context of the present invention, the term organopolysiloxanes is intended to embrace not only polymeric but also dimeric and oligomeric siloxanes.

The radical $R^1$ preferably comprises hydrogen atom and hydrocarbon radicals having 1 to 18 carbon atoms, with particular preference hydrocarbon radicals having 1 to 6 carbon atoms, and especially the methyl radical.

Examples of radical $R^1$ are alkyl radicals, such as the methyl, ethyl, n-propyl, isopropyl, n-butyl, isobutyl, tert-butyl, n-pentyl, isopentyl, neopentyl and the tert-pentyl radical, hexyl radicals, such as the n-hexyl radical, heptyl radicals, such as the n-heptyl radical, octyl radicals, such as the n-octyl radical and isooctyl radicals, such as the 2,2,4-trimethylpentyl and the 2-ethylhexyl radical, nonyl radicals, such as the n-nonyl radical, decyl radicals, such as the n-decyl radical, dodecyl radicals, such as the n-dodecyl radical, tetradecyl radicals, such as the n-tetradecyl radical, hexadecyl radicals, such as the n-hexadecyl radical and octadecyl radicals, such as the n-octadecyl radical, cycloalkyl radicals, such as cyclopentyl, cyclohexyl and 4-ethylcyclohexyl radical, cycloheptyl radicals, norbornyl radicals and methylcyclohexyl radicals, alkenyl radicals, such as the vinyl, allyl, 3-butenyl, 4-pentenyl and 5-hexenyl radical, aryl radicals, such as the phenyl, biphenylyl, naphthyl and anthryl and phenanthryl radical; alkaryl radicals, such as o-, m-, p-tolyl radicals, xylyl radicals and ethylphenyl radicals; aryl radicals, such as the benzyl radical, and also the α- and the β-phenylethyl radical.

The radical R preferably comprises hydrogen atom or substituted or unsubstituted alkyl radicals having 1 to 12 carbon atoms, which can be interrupted by oxygen atoms, and with particular preference comprises hydrogen atom, the methyl and the ethyl radical.

Examples of radical R are the examples specified for $R^1$.

The radical $R^2$ preferably comprises substituted hydrocarbon radicals having 1 to 18 carbon atoms, with particular preference hydrocarbon radicals having 1 to 18 carbon atoms, which are substituted by amino groups and/or derivatives thereof, mercapto groups and also carboxyl groups and/or derivatives thereof.

Examples of radical $R^2$ are hydrocarbon radicals substituted by amino groups and derivatives thereof, such as aminopropyl, aminopropylaminoethyl, cyclohexylaminopropyl or acetylated aminopropyl radicals, mercapto-substituted hydrocarbon radicals, such as the mercapto-n-propyl radical, epoxy-substituted hydrocarbon radicals, such as propyl glycidyl ether radical, hydrocarbon radicals substituted by acrylate and/or methacrylate groups, such as n-propylacrylic ester radical and n-propylmethacrylic ester radical, hydrocarbon radicals substituted by carboxyl groups or derivatives thereof, such as by alkanoic acid radicals, such as the acetic acid radical, the butyric acid radical, the undecenoic acid radical, by acid anhydrides, such as the succinic anhydride radical, by esters, such as the undecene silyl ester radical, hydrocarbon radicals substituted by aldehyde groups, such as propionaldehyde radical, hydroxyl-substituted hydrocarbon radicals, such as primary, secondary and tertiary alcohol radicals, such as the propanol radical, the butanol radical, or aromatic hydroxy-bearing hydrocarbon radicals, such as the phenol radical and the eugenol radical, hydrocarbon radicals substituted by polyglycol groups, such as alkyl polyglycol radicals, an example being the propyl polyglycol radical, hydrocarbon radicals substituted by phosphonato groups, such as phosphonatoalkyl radicals, hydrocarbon radicals substituted by silalactone groups, hydrocarbon radicals substituted by glycoside groups, such as radicals of the formula Z—$R^3$— where Z is a glycoside radical composed of from 1 to 10 monosaccharide units and $R^3$ is alkylene radical or oxyalkylene radical, and also the radicals specified in EP-A-612 759, page 2, line 11 to page 3 up to line 53.

The radical A preferably comprises water-soluble organic dye radicals which contain sulfonic acid groups or sulfonate groups and have azo groups or quinone groups, and/or the complex compound of such radicals with metals.

The radical A can comprise monovalent or polyvalent radicals, so that radical A may also link two or more sil(oxan)yl radicals with one another.

Examples of radical A are

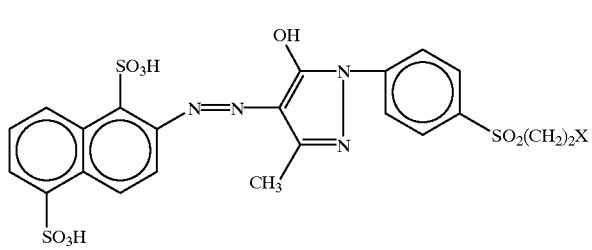

A1

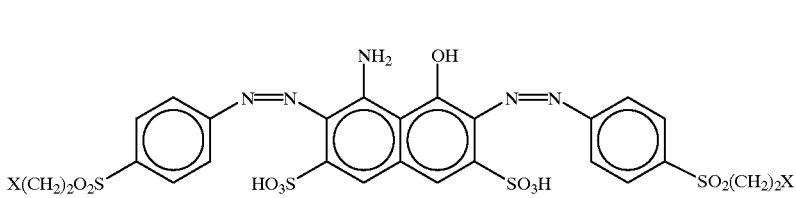

A2

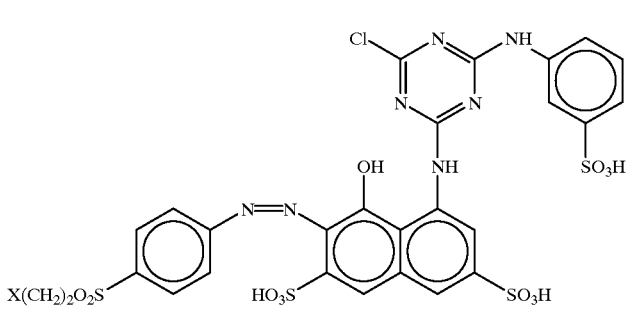

A3

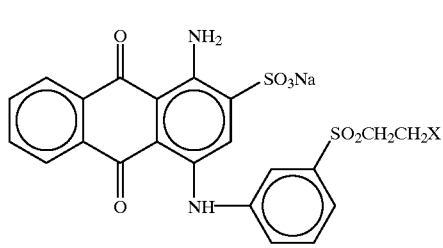

A4

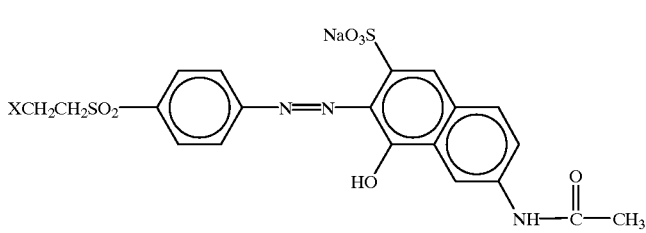

A5 where X is a divalent radical of the formula —YR$^4$— where Y is a radical —O—, —S—, —NH— or —NR$^5$—, R$^4$ is a divalent, substituted or unsubstituted hydrocarbon radical and R$^5$ is a monovalent, substituted or unsubstituted hydrocarbon radical, with the proviso that, in the compound of the invention, Y is connected to the dye radical and R$^4$ is connected to the relevant silicon atom.

The radical R$^4$ preferably comprises divalent, substituted or unsubstituted linear hydrocarbon radicals having 1 to 30 carbon atoms, which can be interrupted by heteroatoms, such as nitrogen, sulfur or oxygen, particular preference being given to substituted or unsubstituted alkylene radicals having 1 to 10 carbon atoms, such as methylene, ethylene, propylene and butylene radical, aminopropylaminoethyl radical, ethylene oxide radical, and alkylene groups substituted by not more than 4 sugar radicals.

The radical $R^5$ preferably comprises monovalent, substituted or unsubstituted hydrocarbon radicals, particular preference being given to substituted or unsubstituted alkyl radicals having from 1 to 10 carbon atoms.

Examples of $R^5$ are the methyl, ethyl, propyl, butyl, cyclohexyl, phenyl and benzyl radical.

The organopolysiloxanes of the invention are prepared using preferably azo or quinonoid dyes which possess one or more identical or different reactive groups.

Examples of such reactive groups which may be attached to the dye molecules are radicals of the formula

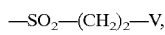

where V has the meaning of halo, sulfato or thiosulfato radical, or triazine radicals, such as those of the formula (III)

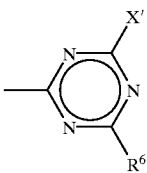

where X' is halo radical, such as fluoro, chloro or bromo, especially chloro radical, and $R^6$ is hydrogen atom or an organic radical.

Examples of the dye molecules employed in accordance with the invention are:

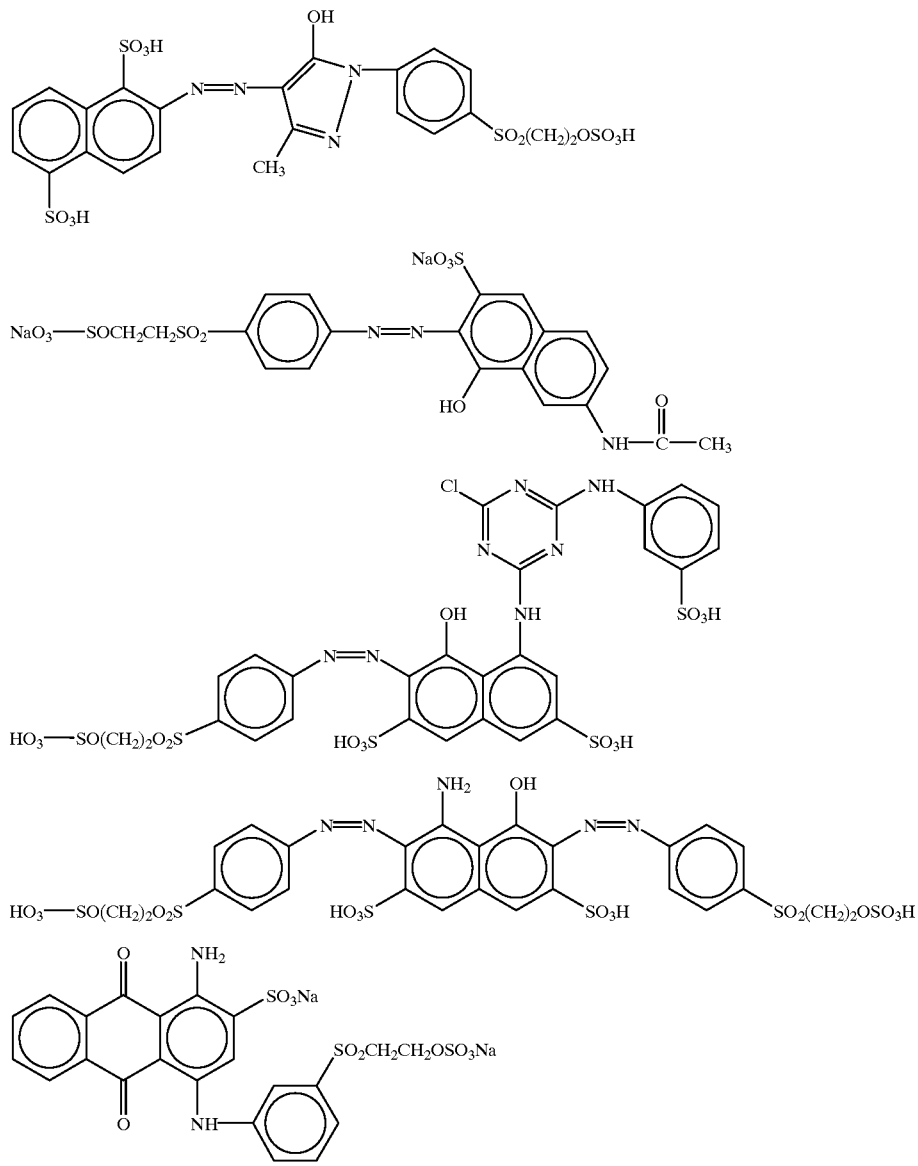

The dyes employed in accordance with the invention are commercially customary products and/or can be prepared by methods common in organic chemistry. For example, the dyes designated as concrete examples are obtainable commercially from the company DYE Stars Darmstadt (Remazol® series) or from the company Reactasil.

The organopolysiloxanes of the invention are preferably those consisting of units of the formula (I), the sum of a+b+c+d being 2 in preferably at least 50%, with particular preference at least 80% and especially at least 90% of all siloxane units, in each case with the proviso that there is at least one radical A per molecule and that, in units of the formula (I) where C is other than 0, d is 0.

With particular preference, the organopolysiloxanes of the invention comprise those of the formula (II)

$$R^1_3SiO(SiA_2O)_e(SiR^1_fR^2_{2-f}O)_g(R^2_mR^1_{2-m}SiO)_h(R^1_jAR^2_{1-j}SiO)_k-SiR^1_3$$

in which $R^1$, $R^2$ and A are as defined above, f is 0 or 1, preferably 1, j is 0 or 1, preferably 1, m is 0, 1 or 2, preferably 0, e is 0 or an integer from 1 to 100, g is 0 or an integer from 1 to 100, h is 0 or an integer from 1 to 1000, and k is an integer from 1 to 100, with the proviso that (e+g)<(h+k)/10 and the units indicated in formula (II) can be distributed randomly in the siloxane molecule.

The viscosities of the organopolysiloxanes of the invention range from preferably 100 $mm^2/s$ up to waxlike substances which are solid at room temperature. Particular preference is given here to the viscosity range between 1000 $mm^2/s$ and 20,000 $mm^2/s$ and to the range of the organopolysiloxanes which at room temperature are waxlike solids.

The dye content of the organopolysiloxanes of the invention is preferably from 0.1 to 80 percent by weight (based on the overall weight), with particular preference from 1 to 15 percent by weight and, in particular from 5 to 10 percent by weight Examples of the organopolysiloxanes of the invention, where Me is methyl radical, are as follows:

Example I: x = 1; y = 55; z = 2 to 3;

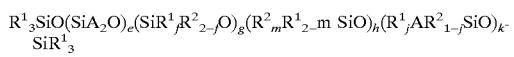
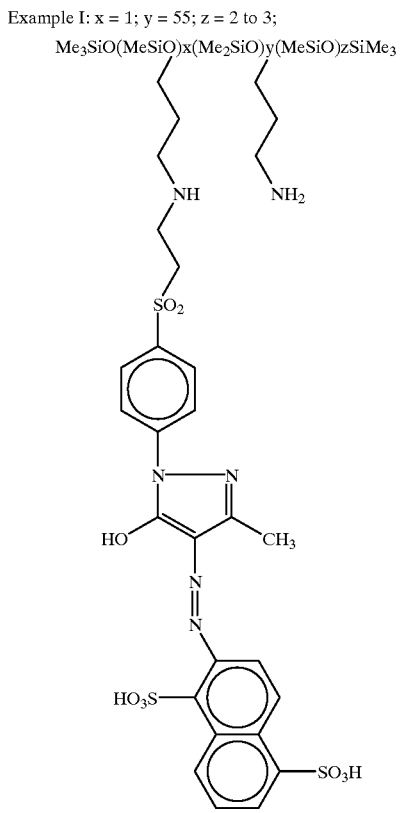

-continued
Example II:
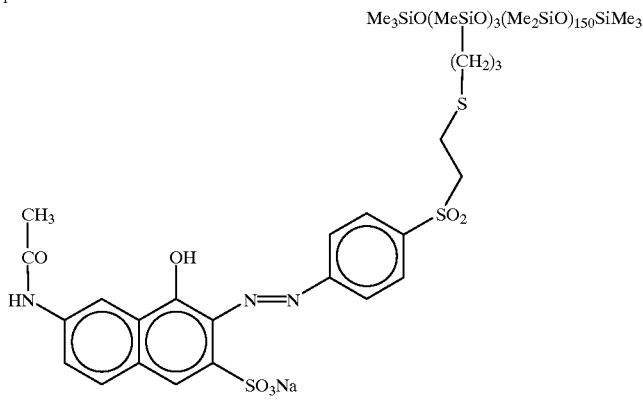
Example III: x = x' = 2; y = 55, z = 1 to 2
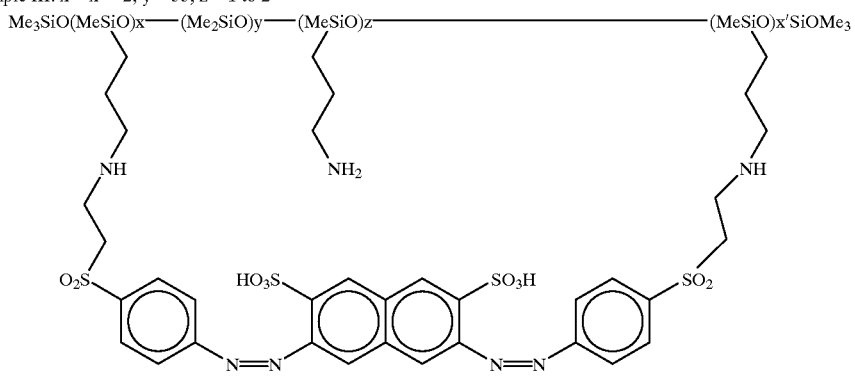
Example IV: x = 2; y = 100, z = 1 to 2
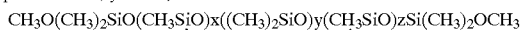
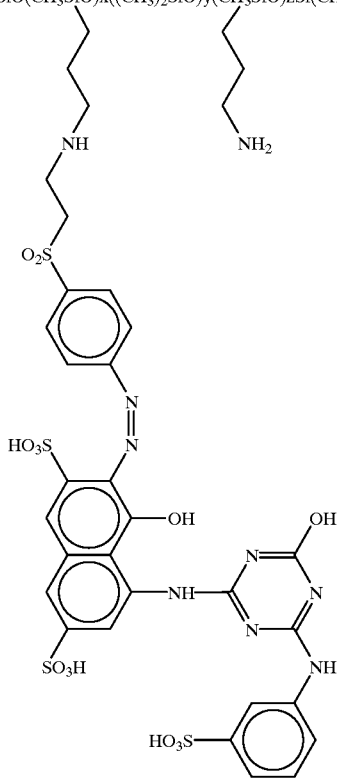

-continued

Example V: x = 3, y = 150

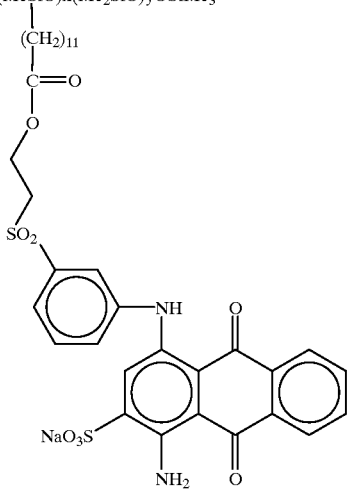

The colored organopolysiloxanes of the invention have the advantage that in addition to the covalently bonded dye radicals they may also contain further functional groups which may give the compound further properties in addition to the color, such as substantivity and hydrophobicity, for example.

The colored organopolysiloxanes of the invention also have the advantage that they are stable: that is, they are stable for at least 1 year at room temperature under the pressure of the surrounding atmosphere.

A further advantage of the colored organopolysiloxanes of the invention is that hydrophobic systems, such as silicone rubber compounds, for instance, can be colored very easily.

The colored organopolysiloxanes of the invention comprising units of the general formula (I) can be prepared in a variety of ways depending in each case on the functional groups of the dye molecules.

The synthesis of the colored organopolysiloxanes of the invention is based in particular on the reaction of the reactive groups attached covalently to the dye molecule, and selected from the group consisting of halogenated triazine radicals, such as those of the formula (III), or radicals of the formula $—SO_2—(CH_2)_2—V$ where V is as defined above, and the intermediates thereof that may be formed during the reaction, such as $—SO_2—CH=CH_2$, with those functional groups of the organopolysiloxanes employed in accordance with the invention that are suitable for reaction, such as aminoalkyl radicals, carboxylic acid radicals or mercaptan radicals.

The present invention additionally provides a process for preparing organopolysiloxanes with dye radicals, which comprises reacting water-soluble organic dyes containing sulfonic acid groups and/or sulfonate groups, and/or the complex compound of such dyes with metals, having reactive groups which are attached covalently to the dye molecule and are selected from the group consisting of halogenated triazine radicals or radicals of the formula $—SO_2—(CH_2)_2—V$ where V is as defined above, and the intermediates thereof that may be formed during the reaction, with organopolysiloxanes which carry amino, carboxyl, mercapto, anhydride, primary, secondary or tertiary carbinol, glycosido, phenol, epoxy, aldehyde, polyglycol, phosphonato, silalactone, acrylate and/or methacrylate groups.

Examples of the dyes employed in the process of the invention have already been indicated above.

The organopolysiloxanes employed in accordance with the invention can comprise any desired organopolysiloxanes, including those known today, such as, for instance, those comprising units of the formula $$R^1_a(RO)_bR'_{c'}R^2_dSiO_{(4-a-b-c'-d)/2} \qquad (I')$$

in which

R, $R^1$, $R^2$, a, b and d are as defined above, R' can be identical or different and is an amino, carboxyl, mercapto, anhydride, primary, secondary or tertiary carbinol, glycosido, phenol, epoxy, aldehyde, polyglycol, phosphonato, silalactone, acrylate or methacrylate radical and c' is as defined for c, with the proviso that the sum of a, b, c' and d is less than or equal to 3, the organopolysiloxanes have at least one radical R' per molecule, and, in the units of the formula (I') where c' is other than 0, d is 0.

Examples of radicals R' are the radicals specified above for the radical $R^2$, preference being given to amino-substituted hydrocarbon radicals and their derivatives, such as aminopropyl, aminopropylaminoethyl radical and cyclohexylaminopropyl radical, and to hydrocarbon radicals substituted by carboxyl groups and/or derivatives thereof, such as by alkanoic acid radicals, such as the acetic acid radical, the butyric acid radical, the undecenoic acid radical, by acid anhydrides, such as the succinic anhydride radical, and by esters, such as the undecene silyl ester radical, and particular preference being given to amino-substituted hydrocarbon radicals and their derivatives, such as aminopropyl, aminopropylaminoethyl radical and cyclohexylaminopropyl radical.

The preferred and particularly preferred species of the organopolysiloxanes employed in accordance with the invention of course comprise analogous structures to those already described above in connection with the organopolysiloxanes of the invention.

The organopolysiloxanes employed in accordance with the invention have a viscosity of preferably from 50 to 50,000 mm²/s, with particular preference from 200 to 15,000 mm²/s, in each case at 250° C.

The organopolysiloxanes employed with particular preference in accordance with the invention comprise especially those having an amine number of from 0.01 to 10.0, the amine number corresponding to the number of ml of 1 N HCl required to neutralize 1 g of substance.

The organosilicon compounds employed in accordance with the invention are commercially customary products and/or can be prepared by the methods common in silicon chemistry.

In principle, the reaction according to the invention can be a nucleophilic addition reaction, nucleophilic substitution on the aromatic heterocycle, and sulfoimide formation, and can be illustrated specifically using the following examples:

1) Nucleophilic Addition Reaction

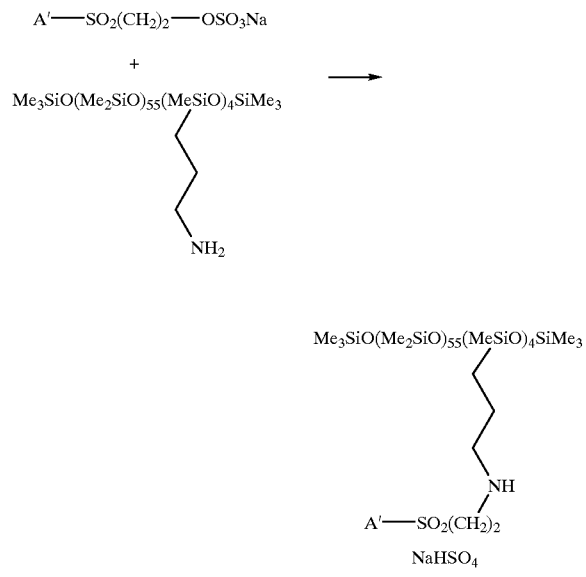

where A' is the chromophoric moiety and Me is methyl radical.

2) Nucleophilic substitution on the aromatic heterocycle

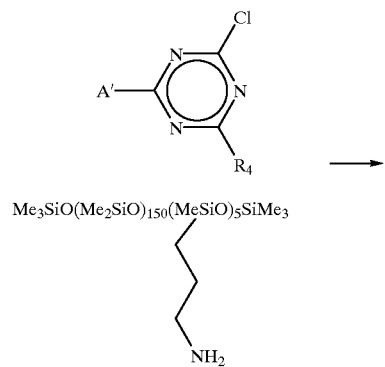

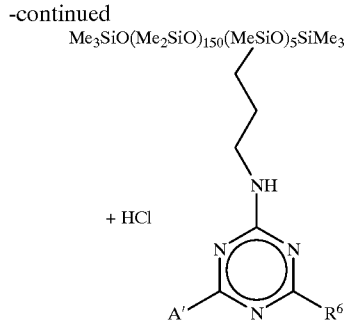

where A' is the chromophoric moiety, $R^6$ is as defined above and Me is methyl radical.

3) Sulfoimide Formation

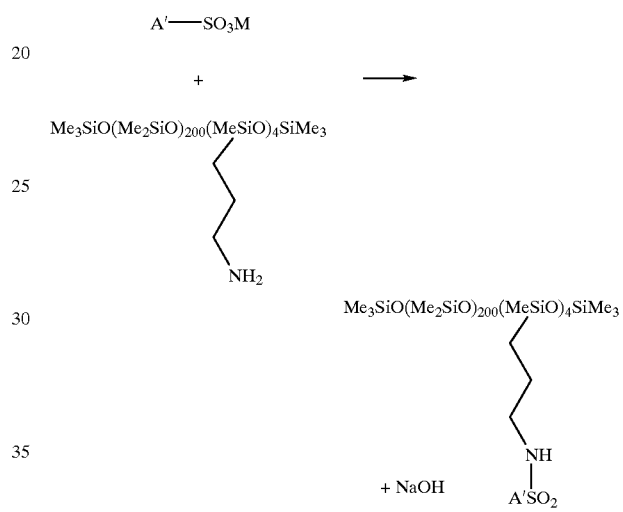

where A' is as defined above and me is methyl radical.

In the reaction according to the invention, dye is used in amounts of preferably from 0.1 to 80 percent by weight, with particular preference from 0.1 to 10 percent by weight and, in particular, from 2 to 5 percent by weight, based in each case on the overall weight of organopolysiloxane employed; the molar amount of dye must not be than 95 mol % of the above-described functional groups in the organopolysiloxane employed in accordance with the invention.

The reaction according to the invention can be carried out in the presence or absence of catalysts, their presence being preferred.

If catalyst is employed, it can comprise acidic or basic catalysts, acidic catalysts being preferred.

Examples of bases which can be employed as a catalyst for the reaction according to the invention are primary and secondary amines, alkali metal alkoxides in aqueous solution, and alkaline earth metal hydroxides and oxides in aqueous solution.

Examples of acids which can be employed as catalyst for the reaction according to the invention are mineral acids and carboxylic acids, preferably carboxylic acids having a $C_0$ to $C_6$ alkyl radical, and with particular preference formic acid and acetic acid.

The acids can be employed in bulk or in solution. If they are employed in solution, water is the particularly preferred solvent.

The catalyst can also be attached covalently to the organopolysiloxane employed in accordance with the invention, such as carboxylic acids or carboxylic anhydrides—in this case, succinic anhydride is particularly preferred. The acidic catalyst attached covalently to the organopolysiloxane can also be at the same time a reaction partner of the reactive dye, such as carboxylic acids or their anhydrides, for example, succinic anhydride.

If catalyst is employed in the reaction according to the invention, the amounts involved are preferably from 0.1 to 1 percent by weight, based on the overall weight of the starting materials.

The reaction according to the invention can be conducted either as a single-phase reaction or as a two-phase reaction, emulsion systems being possible in the latter case.

Process A

Two-phase reaction with mechanical energy input for homogenization

In this process, the reaction of dye with organopolysiloxane takes place using immiscible solvents or one or both reactants, so that two phases are formed, by means of suitable mixing methods without a catalyst or with basic or acidic catalysis; acidic catalysis is particularly preferred.

The reaction according to the invention in accordance with process A is conducted at a temperature of preferably from 0 to 200° C., with particular preference from 50 to 160° C., in particular from 80 to 130° C., and preferably at the pressure of the surrounding atmosphere, i.e., at from 900 to 1100 hPa. The reaction timees are preferably between 5 minutes and 2 hours, with particular preference between 5 and 15 minutes.

Suitable solvents for the dye employed in accordance with the invention, which are inert relative to the reactive groups of the dye, are organic aprotic solvents, water, aqueous electrolyte solutions, aqueous alkalis, aqueous acids, or aqueous-organic mixtures comprising the abovementioned aprotic organic solvents with aqueous systems.

Preferred aprotic, organic solvents are dimethylformamide and dimethyl sulfoxide.

Preferred aqueous systems are aqueous alkalis and aqueous acids, with particular preference being given to aqueous acids.

The solvent in which the dye employed in accordance with the invention is dissolved comprises preferably water, aqueous alkalis and aqueous acids, with particular preference being given to aqueous acids, such as an aqueous 1–30% strength by weight formic acid solution, for example.

Suitable solvents for the organopolysiloxane employed in accordance with the invention are organic aprotic solvents which are inert relative to the reactants, such as toluene, hexane, cyclohexane or dimeric, oligomeric or polymeric siloxanes, such as hexamethyldisiloxane, which are not miscible with the solvent or with the solvent mixture of the reactive dye employed in accordance with the invention.

In the context of the present invention, the concept of solvent immiscibility relates to a miscibility of not more than 1% by weight at 25° C. under the pressure of the surrounding atmosphere.

In process A according to the invention it is possible to employ all known mixing methods, including continuous mixing methods, which provide for maximum homogenization of the two immiscible phases and therefore create a large internal reaction interface. Suitable methods for dispersing the phases include stirring mechanisms of all kinds, preferably ultrasound probes or ultrasound baths and high-speed stirrers, particular preference being given to high-speed stirrers, such as Ultra-Turrax stirrers (Janke & Kunkel, IKA® Labortechnik, Ultra-Turrax T50 (1100 W 10,000 min$^{-1}$).

Process A of the invention has the advantage that the colored organopolysiloxanes obtained in accordance with the invention require no further workup. Process A has the additional advantage that it can be conducted without solubilizers, such as primary alcohol, and without surface-active substances, such as surfactants.

Process B

Two-phase reaction of dispersions, such as emulsions or microemulsions

The reaction of the starting compounds to give the organopolysiloxanes of the invention can also be conducted in emulsion or microemulsion, the organopolysiloxane employed in accordance with the invention being the dispersed phase in the aqueous liquor and being stabilized by a known method, such as by means of suitable emulsifiers. The reactive dye employed in accordance with the invention is dissolved in a suitable solvent, preferably water or aqueous dilute electrolyte solutions, and is added to the dispersion, or vice versa. The reaction proceeds likewise optionally without a catalyst or under basic or acidic catalysis. With regard to the catalysts, the comments made above apply.

The reaction according to the invention in accordance with process B is conducted at a temperature of preferably from 0 to 100° C., with particular preference from 10 to 50° C. and, in particular, from 20 to 35° C., and preferably at the pressure of the surrounding atmosphere, i.e., at from 900 to 1100 hPa. The reaction times are preferably between 1 and 200 hours, it being possible for the dispersion to be mixed.

The dispersion comprising the organopolysiloxane employed in accordance with the invention can be prepared in any desired manner known to date. In this context, it is possible, for example, to use any emulsifiers which have also been used to date to prepare dispersions, such as nonionic, anionic, cationic or amphoteric emulsifiers.

The dispersions employed in accordance with the invention have a siloxane content of preferably from 1 to 30 percent by weight. The dispersed siloxane phase suitably comprises, in particular, aminoalkyl-containing organosiloxane oils employed in accordance with the invention and having a viscosity of between 100 and 10,000 mm$^2$/s and an amine number of between 0.2 and 2.

After the end of the reaction, the dispersion of the invention comprising organopolysiloxanes can be worked up in accordance with methods known per se, such as by breaking the dispersion with concentrated electrolyte solutions or adding water-soluble polar solvents such as acetone. In this case the oil phase is preferably separated off and subsequently worked up by repeated extraction by shaking with concentrated electrolyte solutions, such as 20% strength by weight sodium chloride solution. The organopolysiloxanes of the invention that are obtained in this way are then preferably dried.

If, however, the dispersions of the invention are to be used further directly, workup can of course be omitted. Any desired colors can be established pretty easily by the simple blending of different-colored dispersions of the invention.

Process B of the invention has the advantage that the colored organopolysiloxanes prepared in accordance with the invention are obtained directly in the form of emulsions and can be applied as such directly, depending on the intended use.

Process C

Single-phase Reaction

The reaction of the starting compounds, according to the invention, to give the colored organopolysiloxanes of the invention can also be conducted homogeneously. In that case the reactive dye employed in accordance with the invention and the organopolysiloxane employed in accordance with the invention are dissolved in a common aprotic organic solvent which is inert with respect to the reactants, or in aqueous-organic solvent mixtures, preferably in dimethylformamide or dimethyl sulfoxide and, with particular preference, in dimethyl sulfoxide. The reaction proceeds likewise optionally without a catalyst, or under basic or acidic catalysis as already described above.

The reaction according to the invention in accordance with process C is conducted at a temperature of preferably from 5 to 100° C., with particular preference from 60 to 80° C., and preferably at the pressure of the surrounding atmosphere, i.e., at from 900 to 1100 hPa. The reaction times are preferably from 15 to 300 minutes.

The colored organopolysiloxanes of the invention can then be isolated, for example, by simple distillative removal of the solvent or the solvent mixture.

Process C of the invention has the advantage that it can be conducted in a simple manner using simple apparatus.

All processes of the invention have the advantage that the organopolysiloxanes of the invention can be prepared in a simple manner, reproducibly and with a very good yield, preferably from 90 to 99%.

The organopolysiloxanes of the invention are preferably prepared in accordance with process A or B, with particular preference in accordance with process A, in each case alone or in combination with an equilibration step.

If desired, the organosiloxanes with dye radicals that are obtained in accordance with the processes of the invention can be equilibrated with organopolysiloxanes (1), preferably selected from the group consisting of linear organopolysiloxanes having terminal triorganosiloxy groups, linear organopolysiloxanes having terminal hydroxyl groups, cyclic organopolysiloxanes, and copolymers of diorganosiloxane units and monoorganosiloxane units, thereby making it possible, for example, to establish the desired molecular weight and also the targeted distribution of the dye groups within the molecule and, if desired, making it possible to introduce further functionalities.

Preferably, the linear organopolysiloxanes with terminal triorganosiloxy groups that are employed are those of the formula

  (III), the linear organopolysiloxanes containing terminal hydroxyl groups that are employed are those of the formula

  (IV), the cyclic organopolysiloxanes employed are those of the formula

  (V)

and the copolymers employed are those comprising units of the formulae

where

R$^7$ can in each case be identical or different and is as defined for R, u is 0 or an integer from 1 to 1500, v is 0 or an integer from 1 to 1500, and t is an integer from 3 to 12.

The proportions of the dye-group-containing organopolysiloxanes prepared in accordance with the invention and the organopolysiloxanes (1) employed in the equilibration, if conducted, are determined solely by the desired proportion of the dye groups in the organopolysiloxanes that are produced in the equilibration, which is carried out if desired, and by the desired average chain length.

For the equilibration carried out if desired it is preferred to employ basic catalysts which promote the equilibration. Examples of such catalysts are benzyltrimethylammonium hydroxide, tetramethylammonium hydroxide, alkali metal hydroxide and alkaline earth metal hydroxide in methanolic solution, and silanolates. Preference is given here to alkali metal hydroxides, which are used in amounts of preferably from 50 to 10,000 ppm by weight (parts per million), in particular from 500 to 2000 ppm by weight, based in each case on the overall weight of the organosilicon compounds employed.

The equilibration which is carried out if desired is preferably conducted at from 50 to 150° C., with particular preference from 70 to 120° C. and, in particular, from 80 to 100° C., and preferably under the pressure of the surrounding atmosphere, i.e., between 900 and 1100 hPa. It can also be conducted at higher or lower pressures, however.

The equilibration can be carried out if desired in a water-immiscible solvent, such as toluene, although this is not preferred. If such organic solvents are employed, however, then preference is given to amounts of from 5 to 20 percent by weight, based on the overall weight of the organosilicon compounds employed.

The catalyst can be deactivated before the mixture obtained in the equilibration of the invention is worked up.

The organopolysiloxanes of the invention with covalently attached dye molecules, in bulk, in solution or in the form of dispersions, can be employed wherever there is a requirement simultaneously for the properties of organopolysiloxanes, such as hydrophobicization, dirt repellence, protection, soft feel, etc., in combination with coloration, such as, for example, in the field of cosmetic applications, especially in connection with haircare, for the finishing, dyeing and care of textiles, and in the care of coatings, such as for automotive finishes, for example.

Furthermore, the organopolysiloxanes of the invention can be used for coloring organosilicon compounds of all kinds, since owing to the covalent attachment of the dye to a siloxane molecule there is no incompatibility with other organosilicon compounds. For instance, silicone oils, and crosslinkable silicone rubber compounds, can be colored with a homogeneously distributed dye in molecular form which is subsequently unextractable.

In the examples below, all parts and percentages are by weight unless stated otherwise. Unless specified otherwise, the examples below are conducted at the pressure of the surrounding atmosphere, i.e., at about 1000 hPa, and at room temperature, i.e., at about 20° C. or at the temperature which is established when the reactants are combined at room temperature without additional heating or cooling. All viscosities specified in the examples should be taken as relating to a temperature of 25° C.

EXAMPLE 1

85 g of an aminopropylaminoethyl-functionalized, trimethylsilyl-terminated silicone oil of the type described in Table 1 are placed in a glass beaker. 1.5 g of 85% strength formic acid are incorporated by dispersion over 5 minutes using an Ultra-Turrax. This is followed by the addition of the amount of dye specified in Table 1, in each case dissolved in 5 g of water, which is worked in over 15 minutes using the Ultra-Turrax (Janke & Kunkel, IKA Labortechnik Ultra- Turrax T 50 1100 W 10,000 revolutions/min). Removal of the residual water by distillation gives colored silicon fluids which over a period of months show no flocculation or dye precipitation.

b) Dissolved in 10 g of water
c) No extraction test with water
d) 10% strength solution in toluene In Examples 1a, 1f, 1g and 1h the dye employed is

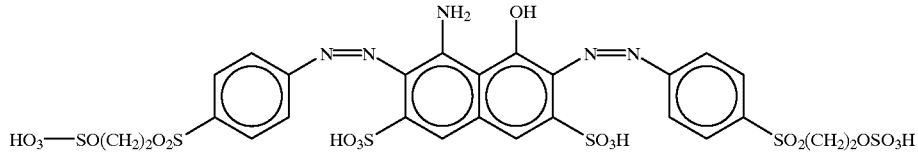

which is obtainable commercially under the tradename Remazol Black GF® from the company Dye Stars, Darmstadt.

In Examples 1b, 1c, 1e, 1f and 1i, a dye is employed which contains sulfatovinylsulfonic acid groups and is obtainable commercially under the tradename Remazol Yellow GF® from the company Dye Stars, Darmstadt.

In Examples 1d and 1j the dye employed is

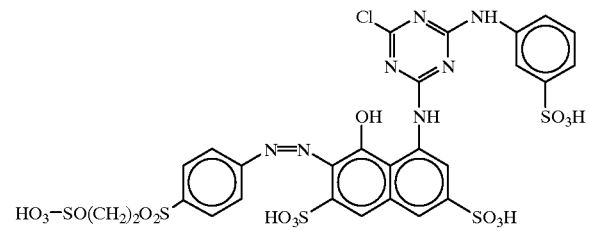

which is obtainable commercially under the tradename Levafix Brilliant Red® from the company Dye Stars, Darmstadt.

EXAMPLE 2

85 g of a functionalized silicone oil terminated with trimethylsilyl groups, of the type identified more closely below, are placed in a glass beaker. Using the Ultra-Turrax described in Example 1, the catalyst in Examples 2a, 2b and 2e is incorporated by dispersion for about 5 minutes. This is followed by the addition of the amount of dye specified in Table 2, in each case dissolved in 5 g of water, which is incorporated over 15 minutes using the Ultra-Turrax. Removal of the residual water by distillation gives colored silicone oils which over months show no flocculation or dye precipitation whatsoever.

TABLE 1

| Example | Amine number of the amine oil employed | Viscosity of the amine oil [mm² /s] | Reactive dye employed | Viscosity of the colored siloxane product [mm² /s] | Extracta ble[a] dye content |
|---|---|---|---|---|---|
| 1a | 0.21 | 5500 | 0.785 g Remazol Black GF ® | 5470 | 2 ppm |
| 1b | 0.21 | 5500 | 0.785 g Remazol Yellow GF ® | 6100 | 5 ppm |
| 1c | 0.21 | 5500 | 3.14 g Remazol Yellow GF ® | 6830 | 12 ppm |
| 1d | 0.21 | 5500 | 0.785 g Levafix Brilliant Red ® | 5940 | 3 ppm |
| 1e | 0.59 | 1230 | 2.24 g Remazol Yellow GF ® | 170,000 | 7 ppm |
| 1f | 0.21 | 5500 | 0.393 g Remazol Black GF ® 0.393 g Remazol Yellow GF ® | 7000 | 2 ppm |
| 1g | 0.23 | solid[d] | 0.936 g Remazol Black GF ® | solid | <0.1 ppm |
| 1h | 11.58 | 3440 | 9.95[b] g Remazol Black GF ® | 38,000 | water-soluble[c] |
| 1i | 11.58 | 3440 | 9.95[b] g Remazol Yellow GF ® | 4400 | water-soluble |
| 1j | 11.58 | 3440 | 9.95[b] g Levafix Brilliant Red ® | 5870 | water-soluble | a) To determine the extractable dye content, 1 g of each reaction product is dissolved in 25 g of an oligomeric siloxane and is extracted by shaking with 42 g of 20% strength by weight sodium chloride solution. For none of the samples is it possible by UV spectroscopy to detect in the aqueous phase any fraction which can be washed out upon the second extraction by shaking; in other words, the extractable dye content is less than 0.1 mg/l.

TABLE 2

| Example | Amine oil employed | Viscosity of the amine oil [mm² s] | Reactive dye employed | Viscosity of the colored siloxane product [mm² /s] | Extract able[a] dye content |
|---|---|---|---|---|---|
| 2a | A[b] | 5300 | 5.03 g Remazol Black GF ® | solid | <0.1 ppm |
| 2b | B[b] | 158 | 3.0 g Remazol Black GF ® | | <0.1 ppm |
| 2c | C | 840 | 0.85 g Remazol Black GF ® | 820 | <0.1 ppm |

TABLE 2-continued

| Example | Amine oil employed | Viscosity of the amine oil [mm² s] | Reactive dye employed | Viscosity of the colored siloxane product [mm²/s] | Extractable[a] dye content |
|---|---|---|---|---|---|
| 2d | D[c] | 150 | 14.4 g Remazol Black GF ® | solid | water-soluble |
| 2e | E[b] | 13,600 | 3.0 g Remazol Black GF ® | 15,600 | 15 ppm |

[a] To determine the extractable dye content, 1 g of each reaction product is dissolved in 25 g of an oligomeric siloxane and is extracted by shaking with 42 g of 20% strength by weight sodium chloride solution. For none of the samples is it possible by UV spectroscopy to detect any fraction which can be washed out upon the second extraction by shaking; in other words, the extractable dye content is less than 0.1 mg/l.
[b] With 1.5 g of 85% strength formic acid as catalyst
[c] 50% strength solution in water The dye indicated in Table 2 is described in Example 1 and the siloxanes A–E below, Me being methyl radical.

Siloxane A:

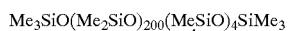

SH

Siloxane B:

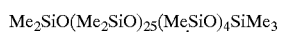

Siloxane C:

$Me_3SiO(Me_2SiO)_{150}(MeSiO)SiMe_3$
|
$(CH_2)_{10}$
|
COOH

Siloxane D:

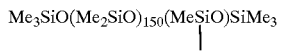
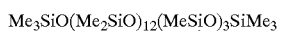
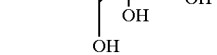

Siloxane E:

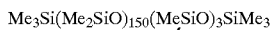
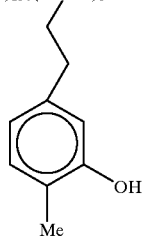

EXAMPLE 3

100 g of the acidic dispersion used, with a pH of 4.5, contain 2% by weight formic acid, 17% by weight aminoethylaminopropyl-functionalized organopolysiloxane having trimethylsilyl end groups and an average chain length of about 150 and the amine number specified in Table 3, and about 10% by weight ethoxylated fatty acid with a chain length distribution between 12 and 18 carbon atoms. The amount of dye indicated in Table 3 is added in each case with stirring at room temperature to this dispersion, the dye being dissolved in 5 g of water in each case. The respective dispersion obtained is then stored at room temperature for 7 days and subsequently broken with 20% strength sodium chloride solution. The resultant isolated, colored silicone oil is washed 10 times with 100 g of 20% strength NaCl solution each time. The residual dye content of the silicone oils, which can no longer be washed out, is then determined by UV-Vis measurement.

TABLE 3

| Example | Amine number of the dispersed amine oil | Reactive dye employed | Residual dye content relative to total dye employed |
|---|---|---|---|
| 3a | 0.6 | 0.42 g Remazol Black GF ® | 95% |
| 3b | 0.6 | 0.42 g Remazol Red 3BS ® | 92% |
| 3c | 0.6 | 0.42 g Remazol Yellow GF ® | 93% |
| 3d | 0.2 | 0.3 g Remazol Black GF ® | 97% |
| 3e | 0.2 | 0.3 g Remazol Red 3BS ® | 96% |
| 3f | 0.2 | 0.3 g Remazol Yellow GF ® | 95% |

The dyes employed in Examples 3a, 3c, 3f and 3d are described in Example 1.

In Examples 3b and 3e a dye corresponding to the radical

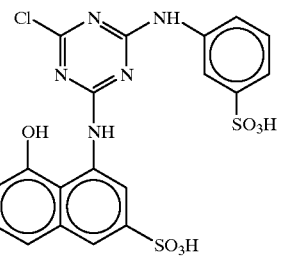

is employed, which is obtainable commercially under the tradename Remazol Red 3BS® from the company Dye Stars, Darmstadt.

EXAMPLE 4

1 g of the dye described in Example 1 and obtainable commercially under the designation Levafix Brilliant Reds® is placed in 9 g of dimethyl sulfoxide. Added to this is a solution of 8.5 g of a trimethylsilyl-terminated aminopropylaminoethyl-functionalized silicone oil having an amine number of 11.58 and a viscosity of 3440 mm²/s in 16 g of dimethyl sulfoxide. As a catalyst, 0.128 g of an aqueous 85% strength formic acid solution is metered in.

The reaction mixture is heated at 80° C. for one hour. Subsequently, the solvent is distilled off at 80° C. under full vacuum. This gives 9.2 g of a red silicone oil which has a viscosity of 12,300 mm²/s and is soluble in water.

EXAMPLE 5

1122 g of an α,ω-dihydroxypolydimethylsiloxane having an average chain length of 35, 78 g of a trimethylsilyl-terminated polydimethylsiloxane having an average chain length of likewise 35, and 18.2 g of a colored silicone oil whose preparation is described in the example indicated in Table 4 and which has been adjusted to a pH of 7 are mixed at room temperature in a 2-litre three-necked flask. Following the addition of the respective equilibration catalyst which is indicated in Table 4, the reactions are conducted at 80° C. for four hours. Following deactivation of the catalyst by neutralization, the individual reaction mixtures are each heated at 80° C. for 2 hours under full vacuum. The viscosities of the resulting colored siloxanes are set out in Table 4.

TABLE 4

| Example | Colored silicone oil prepared in accordance with Example | Equilibration catalyst employed | Viscosity of the product obtained [mm² s] |
|---|---|---|---|
| 5a | 2c | acidic; 150 ppm of phosphonitrile chloride | 7400 |
| 5b | 1i | basic; 1000 ppm of butyltrimethylammonium hydroxide | 9300 |
| 5c | 1j | basic; 1000 ppm of butyltrimethylammonium hydroxide | 24,000 |

To determine the extractable dye content, 1 g of each reaction product is dissolved in 25 g of an oligomeric siloxane and is extracted by shaking with 42 g of 20% strength sodium chloride solution.

For none of the samples is the fraction which can be washed out detectable by UV spectroscopy; in other words, the extractable dye content is less than 20 0.1 mg/l.

What is claimed is:

1. An organopolysiloxane bearing dye radicals, comprising units of the general formula $$R^1{}_a(RO)_b A_c R^2{}_d SiO_{(4-a-b-c-d)/2} \quad (I)$$

in which

R can be identical or different and is hydrogen atom or monovalent, substituted or unsubstituted hydrocarbon radical, $R^1$ can be identical or different and is hydrogen atom or monovalent, SiC-bonded hydrocarbon radical, $R^2$ can be identical or different and is substituted, monovalent, SiC-bonded hydrocarbon radical, A can be identical or different and is a radical of a water-soluble organic dye containing at least one of sulfonic acid groups, sulfonate groups, or metal complexes thereof, a is 0, 1, 2 or 3, b is 0, 1, 2 or 3, d is 0, 1, 2 or 3, and c is 0, 1 or 2, with the proviso that the sum of a, b, c and d is less than or equal to 3, the organopolysiloxanes have at least one radical A per molecule, and, in the units of the formula (I) where c is other than 0, d is 0.

2. An organopolysiloxane with dye radicals as claimed in claim 1, which consists of units of the formula (I).

3. An organopolysiloxane with dye radicals as claimed in claim 1 which is of the formula (II)

$$R^1{}_3SiO(SiA_2O)_e(SiR^1{}_fR^2{}_{2-f}O)_g(R^2{}_m R^1{}_{2-m}SiO)_h(R^1{}_j AR^2{}_{1-j}SiO)_k\text{-}SiR^1{}_3$$

in which $R^1$, $R^2$ and A are as defined above, f is 0 or 1, j is 0 or 1, m is 0, 1 or 2, e is 0 or an integer from 1 to 100, g is 0 or an integer from 1 to 100, h is 0 or an integer from 1 to 1000, and k is an integer from 1 to 100, with the proviso that (e+g)<(h+k)/10.

4. An organopolysiloxane bearing dye radicals as claimed in claim 3, consisting of units indicated in formula (II).

5. The organopolysiloxane of claim 3 wherein units indicated in formula (II) are distributed randomly in the siloxane molecule.

6. An organopolysiloxane with dye radicals as claimed in claim 1, wherein the dye radical content is from 0.1 to 80 percent by weight, based on the overall weight.

7. A process for preparing an organopolysiloxane bearing dye radicals, which comprises reacting water-soluble organic dyes containing at least one of sulfonic acid groups, sulfonate groups, or metal complexes thereof, said organic dyes having reactive groups which are attached covalently to the dye molecule and are selected from the group consisting of halogenated triazine radicals or radicals of the formula $-SO_2-(CH_2)_2-V$ where V is a halo, sulfato, or thiosulfato radical, and the intermediates thereof formed during the reaction, with organopolysiloxanes which carry at least one amino, carboxyl, mercapto, anhydride, primary, secondary or tertiary carbinol, glycosido, phenol, epoxy, aldehyde, polyglycol, phosphonato, silalactone, acrylate or methacrylate groups.

8. The process as claimed in claim 7, wherein the reaction is a two-phase reaction with mechanical energy input for homogenization.

9. The process as claimed in claim 7, wherein the reaction is a two-phase reaction where the siloxane employed in the form of a dispersion.

10. The process as claimed in claim 7, wherein the reaction is a single-phase reaction.

* * * * *